United States Patent [19]

Muller

[11] Patent Number: 5,018,390

[45] Date of Patent: May 28, 1991

[54] METHOD AND APPARATUS FOR MONITORING THE TENSION AND QUALITY OF AN ADVANCING YARN

[75] Inventor: Manfred Muller, Wuppertal, Fed. Rep. of Germany

[73] Assignee: Barmag AG, Fed. Rep. of Germany

[21] Appl. No.: 532,217

[22] Filed: Jun. 1, 1990

[30] Foreign Application Priority Data

Jul. 6, 1989 [DE] Fed. Rep. of Germany ....... 3922244

[51] Int. Cl.$^5$ ............................................... G01N 3/08
[52] U.S. Cl. ......................................... 73/828; 28/187
[58] Field of Search .................. 73/828, 160; 340/677; 57/264, 265, 81; 28/187

[56] References Cited

U.S. PATENT DOCUMENTS

| | | | |
|---|---|---|---|
| 3,729,635 | 4/1973 | Shottenfeld et al. | 28/187 X |
| 3,931,938 | 1/1976 | Hasegawa et al. | 242/45 |
| 3,995,417 | 12/1976 | Lumpert et al. | 57/34 R |
| 4,685,629 | 8/1987 | Sugioka | 242/18 R |
| 4,720,702 | 1/1988 | Martens | 340/677 |
| 4,720,806 | 1/1988 | Schippers et al. | 364/551 |
| 4,774,673 | 9/1988 | Aemmer | 28/187 X |
| 4,828,191 | 5/1989 | Ruge et al. | 242/18 R |

Primary Examiner—Jerry W. Myracle
Attorney, Agent, or Firm—Bell, Seltzer, Park & Gibson

[57] ABSTRACT

A method and apparatus for monitoring the yarn tension at each of a plurality of yarn processing stations is disclosed and wherein the mean value of the monitored tension is continuously determined at each station, and the differential between the monitored value and the mean value is also continuously determined. A first alarm signal is generated whenever the mean value leaves a predetermined tolerance range, and a second alarm signal is generated whenever the differential value leaves a second predetermined tolerance range. These alarm signals are logged, in both number and duration, to provide an indication of the quality of the yarn.

8 Claims, 2 Drawing Sheets

2

METHOD AND APPARATUS FOR MONITORING THE TENSION AND QUALITY OF AN ADVANCING YARN

BACKGROUND OF THE INVENTION

The present invention relates to a method and apparatus for monitoring the tension of an advancing yarn, and which also provides for the qualitative classification of the produced yarn and the produced packages, without interruption of the production.

Martens U.S. Pat. No. 4,720,702 discloses a method for continuously monitoring the yarn tension at each of a plurality of yarn processing stations, and which involves continuously determining the mean value of the monitored tension at each station, and continuously determining the differential between the monitored value and the mean value. An alarm signal is generated whenever the mean value leaves a predetermined tolerance range, and also whenever the differential value leaves a second predetermined tolerance range.

It is an object of the present invention to provide a method and apparatus of the type generally disclosed in the above Martens patent, and which further has the ability to provide for the qualitative classification of the produced yarn and the produced packages, without interruption of the production.

SUMMARY OF THE INVENTION

The above and other objects and advantages of the present invention are achieved in the embodiment illustrated herein by the provision of a method and apparatus which includes the steps of continuously monitoring the value U of the tension of the advancing yarn, while continuously determining the mean value MU of the monitored tension, and while also continuously determining the differential DU between the monitored value and the mean value. A first alarm signal is generated whenever the mean value MU leaves a predetermined tolerance range UMU;LMU for a predetermined time, and a second alarm signal is generated whenever the differential value DU leaves a second predetermined tolerance range UDU;LDU for a predetermined time. In addition, the first and second alarm signals occurring during a predetermined time SR are logged so as to provide an indication of the quality of the yarn.

The logging step preferably includes generating a quality signal QSM (representing a mean value fault) or QSE (representing a differential value fault) in predetermined intervals of repetition TR for as long as either one of the first and second alarm signals is present. Also, the times during which the first alarm signal is present may be summed to provide a first quality signal QLM, and the times during which the second alarm signal is present may be summed to provide a second quality signal QLE, and such that the signals QLM and QLE represent the length of the yarn of inferior quality.

The logging step may include separately counting the first and second alarm signals, and a further alarm signal is preferably generated when the sum of the counted alarm signals exceeds a predetermined limit value. Further, in accordance with one embodiment of the invention, the advancing yarn is wound into a package, and suitable indicia are printed on the package which represents the sum of the counted alarm signals and thus the quality of the yarn in the package.

The number of quality signals may be logged jointly for those generated by deviations of the mean value from its tolerance range and by deviations of the differential signals from their tolerance range. However, it is also possible and preferred to detect as an occurrence and to separately sum by a quality signal a deviation of the mean value from its tolerance range, and a deviation of the differential signal from its tolerance range. In so doing, it is also possible to differently rate the two quality signals of the mean value on the one hand and the differential signal on the other hand. If the total number of one of the quality signals exceeds a certain limiting quality signal, for example 10, an alarm signal can be emitted at the measuring point, or it is possible to cut the yarn and shut down the processing position. The limiting quality signal may be different for the mean value and the differential value.

The damage and the extent of damage of the yarn is not only determined by the number of damaged spots as represented by the number of quality signals, but also by the length of yarn which is damaged. Another object of this invention is to determine the length of yarn of inferior quality. This object is achieved by repeating the quality signal in regular time intervals as long as an alarm signal is present to show that a mean value fault and/or an extreme value fault is present for a time which is longer than a predetermined time TRM for the mean value fault or TRE for the extreme value fault. The total number of quality signals generated in this way during a predetermined time SR is the measure for determining the quality of the package. An alternative embodiment for achieving the above named object is also disclosed, and which provides that the yarn lengths are detected and summed up which are produced under unacceptable conditions, i.e., when the respective tolerance ranges are exceeded by the mean value and/or the differential value, respectively. It is possible to jointly sum the duration of the failure times TM, TE for the deviation of both the mean value and the differential signal from their respective tolerance ranges. However, it is also possible to sum the duration of the failure times for the mean value and the differential value separately from each other and to produce a quality determining signal QDSM, QDSE, when one of the two values exceeds a predetermined limiting total failure time.

BRIEF DESCRIPTION OF THE DRAWINGS

Some of the objects and advantages having been stated, others will become apparent as the description proceeds and when considered in conjunction with the accompanying drawing, in which.

I. a segment of a graph of yarn tension versus time with the yarn tension being indicated by an output signal U from a tension sensor;

II. the mean value MU which results from the yarn tension shown in diagram I;

III. the failure signals A1 or A2, respectively, caused by the mean value MU leaving its tolerance range;

IV. the quality signal QSM caused by the mean value fault alarms A1, A2 as shown in Diagram III;

V. the sum QDSM of the quality signals caused by mean value faults;

VI. yarn length QLM damaged by mean value faults as shown in Diagram III, corresponding to the total time TM during which mean value faults occurred;

VII. the differential value DU which is representative of the difference between the measured output signal U and the mean value MU;

VIII. the failure signals A3 or A4, respectively, caused by the differential value DU leaving its tolerance range, representing extreme value faults;

IX. the quality signal QSE caused by the extreme value fault alarms A3, A4, as shown in Diagram VIII;

X. the sum QDSE of the quality signals caused by extreme value faults.

XI. yarn length QLE damaged by extreme value faults as shown in Diagram VIII, corresponding to the total time TE during which extreme value faults occurred.

DETAILED DESCRIPTION OF THE PREFERRED EMBODIMENTS

Figure 1:
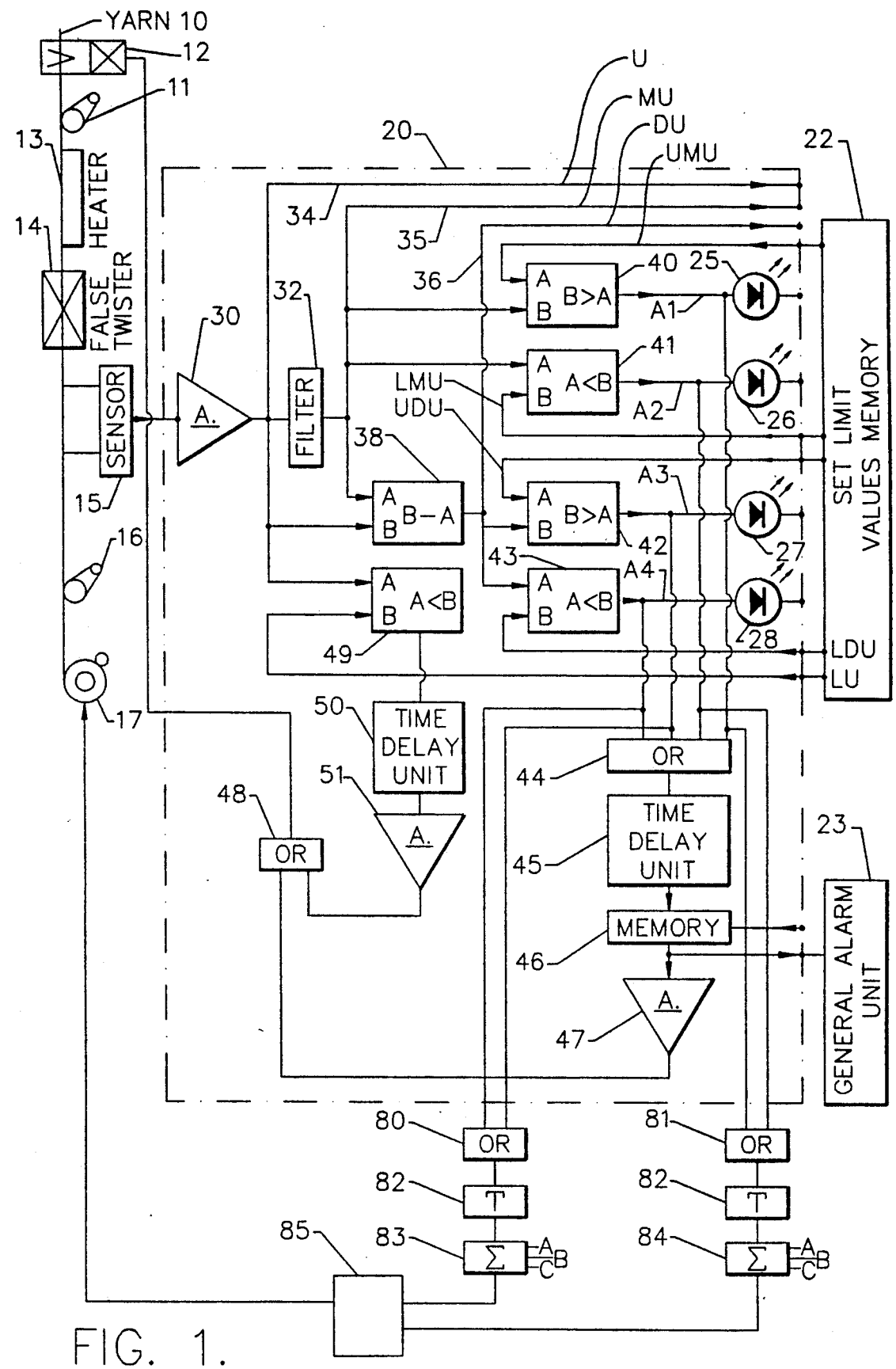
FIG. 1 is a schematic diagram of a yarn processing machine and accompanying circuit which embodies the features of the present invention.

FIG. 1 is a schematic diagram illustrating a yarn processing station and associated control circuitry in accordance with the present invention. The left hand portion of the diagram illustrates a yarn processing station, and wherein a yarn 10 is withdrawn from a supply roll or other source (not shown) by delivery roll 11. The yarn advances past a conventional yarn cutter 12, and then it is guided across and in contact with a heater 13, through a false twister 14, and past a yarn sensor 15. The yarn is withdrawn from the false twisting zone by delivery roll 16 and wound onto a package 17 by means of a conventional winder.

Figure 2:
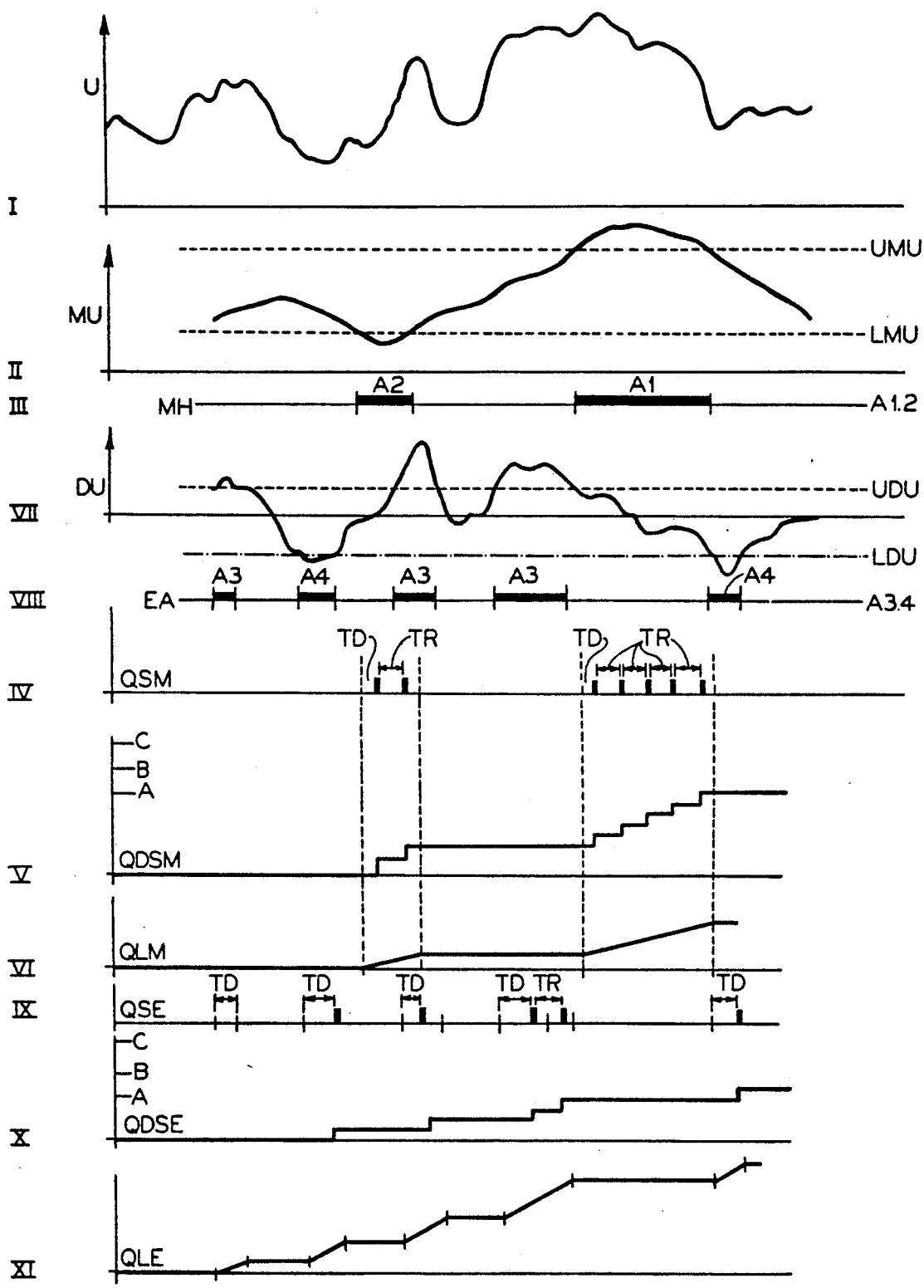
FIG. 2 is s a series of diagrams illustrating.

The output signal U of the sensor 15 is transmitted to a circuit 20, which is illustrated within the dash-dot line of FIG. 2. Circuit 20 is associated with each position of a multi-position false twist machine, and with the yarn sensor 15 of such position. The circuit 20 receives predetermined tolerance values from a set limit values memory 22 which is described below in more detail. Memory 22 is associated with a group of stations of the multiposition texturing machine. Circuit 20 produces one output signal to the yarn cutter 12 and another output signal to a general alarm unit 23 which is also associated with a group of stations. Circuit 20, furthermore, produces output signals to alarm unite 25, 6, 27, 28 which will be described below in more detail. These alarm units are correlated to the associated processing station.

The output signal of yarn sensor 15 is fed to amplifier 30 and then to filter 32. The filter is a circuit containing an induction coil and a capacitor, the circuit having a delay time constant of for example one to three seconds. The output signal of the amplifier 30 is a voltage U which may be fed to a central microprocessor for further processing and calculation via line 34. The output of filter 32 is the mean value MU which may also be fed to a general microprocessor via line 35 for further processing and calculation. On the other side, signal U and signal MU are fed to differential amplifier 38 producing an output signal DU which represents the difference of the input signals U and MU. The output signal DU of the differential amplifier 38 may be fed via line 36 to the central microprocessor for further processing and calculation.

The output signal MU of the filter 32 is furthermore used to produce alarm signals A1 and A2, if the mean value MU leaves the predetermined range of tolerance. The predetermined range of tolerance is defined by the upper limit of the mean value UMU and by the lower limit of the mean value LMU, both of which are stored in the limit values memory 22 and fed to circuit 20 via respective lines. The circuit 20 for this purpose contains triggers 40 and 41. Trigger 40 is fed by the mean value MU and the upper limit of the mean value UMU, and it is designed to produce an output signal A1, if the mean value exceeds the set upper limit of the mean value. Trigger 41 is designed to receive the mean value MU and set lower limit of the mean value LMU as an input signal and to produce an output signal A2, if the mean value Mu is lower than the set lower limit of the mean value.

The circuit 20 also produces alarm signals A3, A4, if the differential signal DU exceeds the predetermined range which is defined by a set upper limit of the differential value UDU and the set lower value of the differential value LDU. The predetermined upper and lower limits are stored in the limit values memory 22 and fed as input signals to triggers 42 and 3, respectively, of the circuit 20. The other input signal to the triggers 42 and 43 is the differential signal DU which is the output of differential amplifier 8 as described above. If the differential signal DU is greater than the set upper limit UDU, trigger 42 produces alarm signal A3. If differential value DU is smaller than the set lower limit LDU, trigger 43 produces alarm signal A4. Each of the alarm signals A1, A2, A3, A4 is fed to either one of the alarm units 25-28 which are associated with this position and which are, e.g., designed as a light emitting diode integrated into the circuit 20. Furthermore, alarm signals A1 to A4 are fed to OR gate 44, delay time unit 45, memory 46 and amplifier 47. The OR gate 44 produces an output signal, if any one of the alarm signals A1 to A4 is present. The delay time unit has a delay constant of about 10 msec, and is designed to prevent an output signal from a transient and irrelevant disturbance of the yarn texturing process, and which could result in the yarn 10 being cut by yarn cutter 12. The memory 46 ensures that a general alarm unit 23, which is associated with a group of stations or with the entire machine, will be able to generate a permanent signal to show that the production is disturbed and/or terminated, The output signal of the memory 46 is also fed to an amplifier 47 and from there to OR gate 48, which receives another signal to be more fully described below. The output signal of the amplifier 47 produces an output signal of the OR gate 48, which in turn is fed to the yarn cutter 12 to cause cutting of the yarn and interruption of the texturizing or drawtexturizing process, as the case may be. The other input signal to OR gate 48 is produced by trigger 49 via delay time unit 50 and amplifier 51. Trigger 49 is fed by the value U representing the measured yarn tension and by a second set value LU stored in set limit value memory 22 and representing the lowest accepted value of the yarn tension. It should be noted that this value LU is preferably set at zero. Trigger 49 produces an output signal, if the measured value U is lower than or equal to the set value LU. The delay time constant of unit 50 may be about 10 msec. The output signal of trigger 49 is, as mentioned above, fed to OR gate 48 and causes yarn cutter 12 to cut the yarn upstream of delivery roll 11, if and when the yarn tension is below a set value or in case of a yarn break between delivery rolls 11 and 16. The apparatus and circuit to the extent described above, generally conforms to that disclosed in the above noted Martens U.S. Pat. No. 4,720,702.

As will be apparent, an alarm signal A1-A4 is produced, when the continuously formed mean value of the measured value and the differential value between the continuously picked up measuring signal and the continuously formed mean value leave their respective tolerance ranges, which are predetermined separately for the mean value and for the differential value.

According to the invention, these occurrences are counted and the number of the occurrences in a predetermined time SR results in a quality determining signal. The time period may, for example, be a winding cycle or a portion thereof. Preferably, the quality signals QSM for the deviations of the mean values and the quality signals QSE for the deviations of the differential value from their respective tolerance ranges are determined and counted separately. Subsequently, a quality class or quality classes are determined, by the number QDSM or QDSE, respectively, of quality signals, occurred during the predetermined unit of time SR such as, for example, A-quality for $1<QDSM<10$ and $1<QDSE<50$
B-quality for $10<QDSM$ or $50<QDSE$
C-quality for $10<QDSM$ and $50<QDSE$ The quality of a produced package is thus made dependent on the number of failures which have occurred.

The failures may occur for different periods of time. The longer a failure occurs, the greater is the damaged yarn length. Consequently, it is possible and preferred to include in the quality evaluation not only the number but also the total duration of failures occurred during a predetermined period of time SR. To this end, the failure times may be summed, i.e., the failure times TM of the mean value faults to sum QLM on the one hand, and the failure times TD of the extreme value faults to the sum QLE on the other.

Also these failure times may be used for the classification of quality, or, however, for an alarm or warning signal, or for interrupting a winding process when a preset time limit for QLM and/or QLE is exceeded.

Referring again to FIG. 1 of the drawing, the alarm signals A1 to A4 are fed to OR gates 80 and 81, respectively. More particularly, alarm signals A1 and A2 representing the failure that the mean value has left its permitted range between the upper limiting value and the lower limiting value, are fed to OR gate 80, whereas the alarm signals A3, A4 representing the failure that the differential signal between the actual measured yarn tension and the mean value has left its predetermined range between the upper and the lower limiting values, are fed to OR gate 81. The output signals of the OR gates 80, 81 are fed via time measuring units 82 to storage means 83 and 84.

Time measuring units 82.1 and 82.2 each have two other inputs. One of the inputs serves to store and preset a delay time TD. The delay time is the time between the first occurrence of an alarm signal A to time measuring units 82.1 and 82.2, and the first occurrence of the output signals QSM or QSE therefrom. The delay time TD can be set differently for each of the time measuring units. The other input of the time measuring units serves for storing a predetermined time of repetition TR. This time of repetition is a preset time, after which the output signal QSM or QSE of the time measuring unit is repeated, if the input signal A thereto lasts longer than said time of repetition TR. This means that every occurrence of a failure exceeding the delay time TD set in the time measuring units 82.1 and 82.2 will cause at least one qualitY signal QSM, QSE to be stored in either one of the storage means 83 or 84.

Another signal QSM, QSE however will be stored in the respective storage means 83 or 84, if an alarm signal fed to the time measuring unit after having been counted, lasts longer than the preset time of repetition TR. That means that each alarm signal causes a first quality signal QSM, QSE, if after its first occurrence the delay time TD has expired and causes a next quality signal QSM, QSE, if it still is present, when the time of repetition has expired after the previous count.

Each of the storage means 83 and 84 has inputs for classification numbers A, B, and C. Each of the classification numbers represents a limited number of quality signals and also a quality classification number. So, for example, the input A may be 10, B may be 20, C may be 30. If the number of quality signals which are summed up in storage means 83 representing mean value faults is less than 10 per winding cycle of one package, the quality classification is A. If the number of failures is between 10 and 20, the quality is B. If the number of failures exceeds 20, the quality is C. Using two OR gates 80, 81 and storage means 83 and 84, each attributed to one kind of failures, it is possible to also classify the quality of the packages according to the kind of deficiencies they have, i.e. deficiencies with regard to the mean value of yarn tension, on the one hand, and to extreme tension values, on the other hand. The output signals from storage means 83, 84 are fed to a marking device 85, for example, a printer for printing quality indicia for the package. It is evident that further criteria of quality classification may be derived from either one of the alarm signals or either group of the alarm signals A1 to A4.

It is furthermore provided, that the output signal from OR gates 80, 81 are fed to integrating units 86, 87 measuring the time during which the respective output signal A of the OR gate 80 or 81 is present. The measured time (deficiency time DT) also represents the yarn length which has been produced and wound up, while a respective one of a mean value failure or an extreme value failure was present. Each of the integrating units 86, 87 has an input for setting and storing a time limit or a yarn length limit LT. If the deficiency time DT stored to the integrating unit exceeds the set time limit LT, an output signal QLM or QLE is caused which may be fed to the marking device 85, showing that more than a permitted range of yarn length is of inferior quality.

With respect to the outputs of storage means 83, 84 and integrating units 86, 87, it should be mentioned that the output signal of either one of these units can also be fed to the OR gate 48 for causing the yarn to be cut by cutter 12, once a predetermined limit of quality signals or deficiency time is exceeded.

As stated above, diagram I of FIG. 2 represents a segment of a graph of yarn tension versus time with the yarn tension being indicated by an output signal U from a tension sensor as shown in FIG. 1. The mean value MU is shown in diagram II. The mean value is determined by supplying the tension signal U to an electrical filter having a relatively long time distance such as filter 32 in FIG. 1.

Diagrams III to VI show the steps of quality evaluation with respect to the mean value faults as per this invention.

As shown in Diagram II, the segment of the mean value during the time as represented by Diagram II exceeds one time the preset lower limit LMU and causes the alarm signal A2 and exceeds another time the upper limit UMU and causes the alarm signal A1 (see FIG. 1)Alarm.

The alarm signals A1 and A2 are fed to OR gate 81, the output of which causes time measuring device 82.1 to run. This is shown in Diagram IV. After the preset delay time TD has expired, time measuring device 82.1 gives an output signal QSM represented in Diagram IV.

The output signal QSM is repeated after a preset time interval TR. For example, that during alarm signal A1 the first signal is generated after expiration of the delay time TD and four other signals QSM are generated each after expiration of one repetition interval TR.

The QSM signals are fed to storage unit 84 for summing up all of the QSM signals to a quality determining signal for the mean value faults QDSM which is shown in Diagram V. The quality determining signal QSM exceeding one of the preset limits A, B, C determines the quality.

The output signal of OR-gate 81 as shown in Diagram III is also fed to integrating device 86. Thereby, a quality signal is generated, a graph of which is shown in Diagram VI. This quality signal QLM is the total time during which one of the alarm signals A1, A2 was generated. As the yarn speed is constant, this signal QLM also corresponds to the length of yarn which was produced, while a mean value fault was present. This length of yarn is more or less damaged, and the length of yarn therefore also determines the quality. Therefore, the QLM signal is also fed to the printer 85.

The measured yarn tension U and the mean value of the yarn tension as formed by filter 32 is also fed—as shown in FIG. 1—to the triggers 42, 43 and a differential signal DU is formed. The segment of a graph shown in Diagram VII represents the difference DU between the measured value U and the mean value MU. As can be seen from Diagram VII this differential value DU sometimes exceeds the upper limit UDU and the lower limit LDU preset for the value DU. That means that the extreme value of the yarn tension represented by the output signal U exceeds a permitted range. Therefore, signals A3 or A4 are generated, respectively, representing such an extreme value fault. These alarm signals A3, A4, respectively, are shown in Diagram VIII. Alarm signals A3, A4 are fed via OR gate 80 to time measuring device 82.2. Time measuring device 82.2 has two inputs as described with reference to device 82.1. The inputs of time measuring device 82.2, however, can be set differently from that one of time measuring device 82.1. Performance, however, is identical and therefore reference is made to the above description. The time measuring device 82.2 gives a quality signal QSE after expiration of the delay time TD and furthermore another quality signal QSE after each interval TR for the whole time during which one of the alarm signals A3, A4 is present. Integrating device 83 sums up all of these quality signals QSE to the output signal QDSE determining the quality of the package with respect to extreme value faults occurred during the preset time SR. The signal QDSE is shown in Diagram X.

The output signal of OR gate 80 can also be given to integrating device 87 for integrating the total time during which one of the alarm signals A3, A4 was present. Thereby a quality signal QLE is generated representing the length of yarn damaged by extreme value faults. This is shown in Diagram XI.

In the drawings and specification, there has been set forth a preferred embodiment of the invention, and although specific terms are employed, they are used in a generic and descriptive sense only and not for purposes of limitation.

That which is claimed is:

1. A method of monitoring the tension of an advancing yarn, and comprising the steps of
continuously monitoring the value (U) of the tension of the advancing yarn, while continuously determining the mean value (MU) of the monitored tension, and while also continuously determining the differential (DU) between the monitored value and the mean value, generating a first alarm signal whenever the mean value (MU) leaves a predetermined tolerance range (UMU;LMU) for a predetermined time, and generating a second alarm signal whenever the differential value (DU) leaves a second predetermined tolerance range (UDU;LDU) for a predetermined time, and logging of the first and second alarm signals occurring during a predetermined time (SR) so as to provide an indication of the quality of the yarn.

2. The method as defined in claim 1 wherein the logging step includes generating a quality signal (QSM or QSE) in predetermined intervals of repetition (TR) for as long as either one of said first and second alarm signals is present.

3. The method as defined in claim 1 or 2 comprising the further steps of summing the times during which the first alarm signal is present to provide a first quality signal (QLM), and/or summing the times during which the second alarm signal is present to provide a second quality signal (QLE), and such that the first and second quality signals represent the length of the yarn of inferior quality.

4. The method as defined in claim 1 wherein the logging step includes separately counting the first and second alarm signals, and generating an alarm signal whenever the number of either of the first and second alarm signals exceeds a respective limit number.

5. The method as defined in claim 1 comprising the further steps of winding the advancing yarn into a package, and printing indicia on the package which represent the sum of the logged alarm signals and thus the quality of the yarn in the package.

6. A yarn processing machine including means for monitoring the tension of an advancing yarn, and comprising sensor means for continuously monitoring the value (U) of the tension of the advancing yarn, first circuit means operatively connected to said sensor means for continuously determining the mean value (MU) of the monitored tension, for continuously determining the differential (D) between the monitored value and the mean value, for generating a first alarm signal whenever the mean value (MU) leaves a predetermined tolerance range (UMU;LMU) for a predetermined time, and for generating a second alarm signal whenever the differential (D) leaves a second predetermined tolerance range (UDU;LDU) for a predetermined time, and second circuit means for logging the number of alarm signals occurring during a predetermined time so as to provide an indication of the quality of the yarn.

7. The yarn processing machine as defined in claim 6 wherein said second circuit means includes means for separately counting said first and second alarm signals, and for generating a further alarm signal whenever either or both of said first and second alarm signals exceeds a predetermined limit value.

8. The yarn processing machine as defined in claim 6 further comprising means for winding the yarn into a package, and for printing indicia on the package which represents the sum of the logged alarm signals and thus the quality of the yarn in the package.

* * * * *

UNITED STATES PATENT AND TRADEMARK OFFICE
CERTIFICATE OF CORRECTION

PATENT NO. : 5,018,390
DATED : May 28, 1991
INVENTOR(S) : Manfred Müller

It is certified that error appears in the above-identified patent and that said Letters Patent is hereby corrected as shown below:

Column 2, line 54, delete "s"

Column 3, line 41, "6" should be -- 26 --

Column 4, line 16, "3" should be -- 43 --

Column 4, line 19, "8" should be -- 38 --

Column 5, line 64, "qualitY" should be -- quality --

Column 6, line 68, delete "Alarm"

Signed and Sealed this

Twenty-ninth Day of December, 1992

*Attest:*

DOUGLAS B. COMER

*Attesting Officer*     *Acting Commissioner of Patents and Trademarks*